(12) United States Patent
Rice et al.

(10) Patent No.: US 8,273,382 B2
(45) Date of Patent: *Sep. 25, 2012

(54) SUPPRESSING MICROBIAL GROWTH IN PULP AND PAPER

(75) Inventors: Laura E. Rice, Oak Park, IL (US);
Andrew J. Cooper, Oswego, IL (US);
Robert L. Wetegrove, Winfield, IL (US); Michael V. Enzien, Lisle, IL (US)

(73) Assignee: Nalco Company, Naperville, IL (US)

( * ) Notice: Subject to any disclaimer, the term of this patent is extended or adjusted under 35 U.S.C. 154(b) by 163 days.

This patent is subject to a terminal disclaimer.

(21) Appl. No.: 12/689,742

(22) Filed: Jan. 19, 2010

(65) Prior Publication Data

US 2010/0119620 A1 May 13, 2010

Related U.S. Application Data

(62) Division of application No. 11/341,814, filed on Jan. 27, 2006, now Pat. No. 7,776,363.

(51) Int. Cl.
*A01N 59/08* (2006.01)
*A01N 47/28* (2006.01)
*A61L 2/18* (2006.01)
*D06L 3/00* (2006.01)
*D21C 9/08* (2006.01)
*C01B 11/00* (2006.01)

(52) U.S. Cl. ............... 424/661; 514/588; 8/107; 162/1; 252/187.2; 422/37; 424/665

(58) Field of Classification Search ................ 424/661, 424/665; 514/588
See application file for complete search history.

(56) References Cited

U.S. PATENT DOCUMENTS

| 3,749,672 | A | * | 7/1973 | Golton et al. ............ 252/186.34 |
| 3,767,586 | A | | 10/1973 | Rutkiewic et al. |
| 5,565,109 | A | | 10/1996 | Sweeny |
| 5,942,240 | A | | 8/1999 | Merianos et al. |
| 6,117,817 | A | | 9/2000 | Lindner et al. |
| 6,136,205 | A | | 10/2000 | Dallmier et al. |
| 6,270,722 | B1 | | 8/2001 | Yang et al. |
| 6,478,972 | B1 | | 11/2002 | Shim et al. |
| 6,533,958 | B2 | | 3/2003 | Shim et al. |
| 6,669,904 | B1 | | 12/2003 | Yang et al. |
| 6,710,017 | B2 | | 3/2004 | Unhoch et al. |
| 2002/0003114 | A1 | | 1/2002 | Sweeny et al. |
| 2003/0029612 | A1 | | 2/2003 | Burd et al. |
| 2003/0029812 | A1 | * | 2/2003 | Burns et al. ................... 210/764 |
| 2003/0228373 | A1 | | 12/2003 | Ludensky et al. |
| 2006/0089285 | A1 | * | 4/2006 | Ahmed et al. ................. 510/370 |

FOREIGN PATENT DOCUMENTS

| JP | 31492 | 3/1981 |
| WO | 9734827 | 9/1997 |
| WO | WO01/42145 | 6/2001 |
| WO | WO03/073848 | 9/2003 |

* cited by examiner

*Primary Examiner* — John Pak
*Assistant Examiner* — Nathan W Schlientz
(74) *Attorney, Agent, or Firm* — Benjamin E. Carlsen; Andrew D. Sorenson

(57) ABSTRACT

A composition for anti-microbial effect in a water system such as a pulp and paper processing line with an aqueous slurry. The composition comprises a free chlorine-generating biocide comprising a chlorine source, urea, and an alkali in a concentration sufficient to provide a pH greater than 10, and typically at least pH 11.

14 Claims, No Drawings

SUPPRESSING MICROBIAL GROWTH IN PULP AND PAPER

CROSS REFERENCE TO RELATED APPLICATION

This application is a divisional of U.S. Ser. No. 11/341,814 now U.S. Pat. No. 7,776,363, which is herein incorporated by reference.

BACKGROUND OF THE INVENTION

Oxidants, such as sodium hypochlorite, are routinely used to control microbial growth in paper making systems. Paper pulp, being a mass of wet cellulose and other materials, provides abundant opportunity for the growth of bacteria, fungi, and other microbes, so that a free chlorine-generating biocide is desirably added to the treated system.

While oxidants such as chlorine can provide adequate microbial control, they have a negative effect on optical brighteners, dyes, and the like which are added to the pulp. Also, chlorine that is released in the pulp can cause corrosion of nearby metal components of the processing machinery. The negative effects of chlorine can be reduced by using halogen stabilizers. While Sweeny U.S. Pat. No. 5,565,109 discloses a variety of organic halogen stabilizers, the effectiveness of the process has been unduly low, and the yield of stabilized chlorine species has been unduly low.

By this invention, an improvement is provided with respect to urea and derivatives thereof as a stabilizer of a free halogen source such as sodium or calcium hypochlorite. It has been found that at a pH that is greater than 10, the reaction yield is significantly improved, to provide stabilized halogen (particularly chlorine) in a treated system. Because of the stabilizing action of urea exerted on a free chlorine-generating biocide agent such as sodium hypochlorite, it has been found that improved microbial control can be provided, while minimizing or eliminating the undesirable impact of chlorine on other additives to the wet end of the paper process and the pulp, such as dyes and optical brightening agents. Also, less chlorine-generating agent is required to be added, because of its stabilized form and consequent more gradual release of chlorine, providing a greater antimicrobial effect for improved reduction of microorganisms such as planktonic and sessile bacteria. Also, corrosive effect upon the metal parts of the processing apparatus is reduced by the stabilization provided to free chlorine-generating materials, in accordance with this invention.

DESCRIPTION OF THE INVENTION

By this invention, a composition for antimicrobial effect is provided for industrial water systems such as pulp and paper processing. The composition comprises: a free chlorine-generating biocide comprising a chlorine source; urea and an alkali in a concentration sufficient to provide a pH of greater than 10. Typically, the alkali comprises sodium or potassium hydroxide, but other alkali materials may be used.

Urea is generally of the formula $CH_4N_2O$.

Typically, the amount of urea present in the composition is sufficient to produce a molar ratio of chlorine (as $Cl_2$) to urea in the range of essentially 2:1 to 1:2, in some embodiments a range of 1.5:1 to 1:1.5, with typically substantially equal molar amounts of the two materials being used.

The ingredients cited above may comprise a solution or a dispersion in water, and may be applied to the treated system such as paper pulp, for example in a concentration from 100 to 1 ppm of the free chlorine-generating biocide comprising a chlorine source, from 60 to 0.2 ppm of urea, and from 100 to 1 ppm of alkali, particularly alkali hydroxide such as sodium hydroxide or potassium hydroxide.

In some embodiments, the antimicrobial composition comprising the three components described above may have a pH of at least about 11 or 12.

The urea may be in any commercially available concentration or form. The alkali used is typically sodium hydroxide for reasons of cost, coupled with effectiveness.

Further in accordance with this invention, a method is provided for stabilizing chlorine for use as a biocide in a paper process water system, such as a paper pulp processing system. The process comprises the steps of:

adding, with mixing, a free chlorine source, (such as sodium or calcium hypochlorite) to a point in a stream of the process water system; adding, with mixing, urea or a derivative thereof to a point in the stream of the process water system; and adding, with mixing, an alkali to a point in the stream of the process water system, to cause mixing of the alkali with the chlorine source and the urea, wherein the amount of alkali added is sufficient to achieve a pH of greater than 10 in at least at an area of mixing with the urea and free chlorine source.

Thus, the free chlorine source is stabilized, but in a manner where chlorine is released in a controlled manner, to achieve the benefits described above such as: the need for less free chlorine source, better functioning of additives to the paper process such as optical brighteners and dyes, less vapor phase corrosion effect on metal components of the process line, and the like.

The chlorine source, the urea, and the alkali may all be added to points in the stream of the paper process system which are the same or spaced, but typically adjacent to each other, or all premixed. If desired, the chlorine source and the alkali may be premixed and added to the stream of the paper process system together, and the urea may be separately added to the stream of the paper process system, either at the same location or at a nearby location.

Alternatively, the chlorine source, the urea, and the alkali may all be separately added to the stream of the paper processing system, typically at the same or closely spaced points of the stream.

Other alternatives that may also be used include the addition of the chlorine source as one solution, and the urea and the alkali as another solution.

Another alternative is to add a pair of solutions: one comprising the chlorine source plus some of the alkali, and the other solution comprising urea and the remainder of the alkali.

The chlorine source, the urea, and the alkali may be mixed prior to addition to the treated system. The resulting stabilized product may be stored for a substantial period of time, then added to the treated system when desired.

The free chlorine-generating biocide may comprise any appropriate materials such as calcium hypochlorite, sodium hypochlorite, dichloroisocyanurate, trichloroisocynaurate, dichlorohydantoin, (CAS #118-52-5 and #89415-87-2), and/or molecular chlorine ($Cl_2$).

The chlorine source may comprise a commercially available, aqueous solution of sodium hypochlorite having approximately 5-15 weight percent of chlorine (based on $Cl_2$), plus sufficient sodium hydroxide to provide a pH of preferably at least 11 after reaction with urea, and in some embodiments at least 12.

The urea may comprise an aqueous urea solution in a concentration that is within about 20% of the solubility limit for urea in the solution, at the temperature at which the solution is used.

As stated, the chlorine source and the urea are typically present in a molar ratio of 2:1-1:2, the chlorine being calculated as $Cl_2$, and typically the two ingredients are present in substantially equimolar relation.

In one embodiment, a 30 weight percent urea solution may be blended with a 12.5 weight percent sodium hypochlorite solution containing 2 weight percent sodium hydroxide, in such proportions as to achieve a one to two molar ratio of $Cl_2$ to nitrogen of the urea (the ratio being in favor of nitrogen). This is equivalent to an equimolar chlorine to urea solution. The resulting stabilized-chlorine solution may then be added to the process line as a single, mixed solution.

As stated above, this mixture of components may be added to the treated system and mixed therein, to provide significant antibacterial effect, with reduced or eliminated degradation of additives as described above, and other advantages.

In another aspect of the present invention, paper is produced from a paper process system that includes the addition of the compositions of the present invention to a paper process system.

In another aspect of the present invention, the compositions of the present invention are used in conjunction with one or more optical brighteners. In yet a further embodiment, the optical brighteners are added before or after the addition of the compositions of the present invention.

The following examples are provided for illustrative purposes only, and are not intended to define the invention which is as described in the claims below.

Example 1

We blended 5.0 mL NaOCl (3% as $Cl_2$ in water) with 5.0 mL of an aqueous solution of urea and sodium hydroxide (0.5M urea in 5% NaOH). This yielded a 1:1 molar ratio of chlorine to urea as shown in Table 1. To achieve a 2:1 molar ratio of chlorine to urea we blended 5.0 mL NaOCl (3% as $Cl_2$ in water) with 5.0 mL of an aqueous solution of urea and sodium hydroxide (0.25M urea in 5% NaOH). Halogen residuals were measured using DPD reagent, and were recorded 3 minutes after mixing with the reagent. The results are outlined in Table 1.

TABLE 1

| Solution | pH after mixing | Total Halogen (% Yield) | Free Halogen (% Yield) |
|---|---|---|---|
| NaOCl | 9.8 | 100 | 100 |
|  | 13.0 | 100 | 100 |
|  | 13.5 | 100 | 100 |
| NaOCl:Urea (1:1 mole ratio) | 6.5 | 39 | 2.0 |
|  | 12.4 | 48 | 1.5 |
|  | 13.4 | 64 | 6.0 |
| NaOCl:Urea (2:1 mole Ratio) | 5.6 | 37 | 9.4 |
|  | 8.8 | 117 | 5.9 |
|  | 13.3 | 69 | 32 |

In the presence of urea, side reactions reduce the overall "total halogen", but the yield rises with rising pH. Also, the active chloroureas that remain are more effective antimicrobials, and halogen is stabilized for longer antimicrobial activity in the presence of high organic contamination, as in paper processing. This improves the yield of total halogen (free and combined) and free halogen.

Example 1 shows the benefit of alkali addition in the stabilization reaction between chlorine and urea, where the yield is the amount of total halogen relative to an NaOCl control. Because of the higher yield, less halogen is required to achieve the desired anti-microbial effect under these test conditions. Further examples will show that the benefits of using less halogen include lower cost, less attack on dyes, and lower corrosion of processing equipment. The advantages of increased yield and improved anti-microbial activity are shown in Example 2.

Example 2

Addition of sodium hydroxide to increase pH of a stabilization mixture between chlorine and urea was shown to dramatically increase antimicrobial efficacy of the resulting solution. Two different halogen solutions were created. We blended 5.0 ml. NaOCl (3% as $Cl_2$ in water) with 5.0 ml. of an aqueous solution of urea (0.25M). This yielded a 2:1 molar ratio of chlorine to urea at pH 5.6 as shown in Table 2. We then blended 5.0 mL NaOCl (3% as $Cl_2$ in water) with 5.0 mL of an aqueous solution of urea and sodium hydroxide (0.25M urea in 5% NaOH). This yielded a 2:1 molar ratio of chlorine to urea at pH 13.3 as shown in Table 2. Paper process water was collected from a mill in the Midwestern US producing coated freesheet grades (pH 5.9). Halogen solutions were added to the paper process water at applied doses of 2.5 ppm total chlorine. Bacterial concentrations in the process water samples were determined after 0.5, 4, and 24 hours to determine the efficacy of each halogen solution against bacteria native to the process water sample. The results are outlined in Table 2.

The addition of sodium hydroxide to increase the pH when mixing NaOCl with urea significantly enhanced the yield (as measured by the total chlorine concentration of the resulting solution) by stabilizing the chlorine. This increased yield at high pH meant that less halogen solution was required to apply 2.5 ppm of total chlorine to the paper process water, compared to more needed $Cl_2$ in the solution without added alkali, because the chlorine is stabilized at higher pH. For example, 431 ppm of the chlorine solution at low pH was required for an applied dose of 2.5 ppm chlorine, whereas only 245 ppm of the chlorine solution at higher pH was required for an applied dose of 2.5 ppm chlorine (Table 2).

In addition to having higher total chlorine, the solution containing NaOCl and urea at high pH was more effective at killing bacteria compared the NaOCl and urea solution at low pH. At the four-hour time point in this study, reduction in bacterial concentrations at the same applied chlorine dose were more than 10,000 times greater using the high pH NaOCl and urea solution compared to the low pH solution. At the 24 hour time point in this study, reduction in bacterial concentrations at the same applied chlorine dose were more than 1,000-times greater using the high pH NaOCl and urea solution compared to the low pH solution.

The exhibited combination of higher reaction yield and greatly improved antimicrobial efficacy makes the addition of an alkali source such as sodium hydroxide to the urea and NaOCl reaction a highly desirable improvement to the chlorine stabilization process.

TABLE 2

| Solution | Solution concentration required to apply 2.5 ppm chlorine | Contact time (hours) | Bacteria concentration (log 10 cfu/ml) |
|---|---|---|---|
| NaOCl:Urea at 2:1 molar ratio, pH 5.6 | 431 ppm | 0.5 | 7.0 |
| | | 4 | 7.1 |
| | | 24 | 6.1 |
| NaOCl:Urea at 2:1 molar ratio, pH 13.3 | 245 ppm | 0.5 | 6.6 |
| | | 4 | 2.8 |
| | | 24 | 2.7 |

Example 3

The addition of urea to sodium hypochlorite surprisingly enhances control of filamentous bacteria, which are known to contribute to problematic paper machine deposits. Two biocide solutions were evaluated and included NaOCl and NaOCl mixed with urea at a 1:1 molar ratio. The unstabilized NaOCl solution was 3% as $Cl_2$ in water. To prepare the stabilized chlorine solution we blended 5.0 mL NaOCl (3% as $Cl_2$ in water) with 5.0 mL of an aqueous solution of urea and sodium hydroxide (0.5M urea in 5% NaOH). This yielded a 1:1 molar ratio of chlorine to urea as shown in Table 3. In the case of the stabilized chlorine the NaOCl and urea were mixed prior to introduction to buffered water (pH 7.2) inoculated with approximately $1 \times 10^5$ bacterial filaments/mL of the filamentous test isolate. The filamentous test isolate used in this evaluation was Sphaerotilus natans (ATCC 1529). The Mean Biocidal Concentration was identified as the test chlorine concentration in ppm of total chlorine ($Cl_2$) required for 100% kill of the filamentous test isolate. Results are outlined in Table 3.

TABLE 3

| Solution | Contact Time (hours) | Mean Biocidal Concentration (ppm Total $Cl_2$) S. natans |
|---|---|---|
| NaOCl, pH 9.8 | 0.5 | 5 |
| | 1 | 5 |
| | 3.5 | 5 |
| | 9 | 5 |
| NaOCl:Urea (1:1 mole Ratio), pH 13.4 | 0.5 | 5 |
| | 1 | 5 |
| | 3.5 | 2.5 |
| | 9 | 1 |

Urea significantly enhanced the bactericidal activity of NaOCl against filamentous bacteria. In the presence of urea with adequate contact time, 1 ppm halogen resulted in control of filamentous bacteria comparable to 5 ppm halogen when NaOCl was used alone.

Example 4

This Example shows that the antibacterial efficacy of NaOCl was enhanced when blended with urea prior to addition to a paper process water sample. The unstabilized bleach solution was 3% as $Cl_2$ in water. To prepare the stabilized chlorine solution we blended 5.0 mL NaOCl (3% as $Cl_2$ in water) with 5.0 mL of an aqueous solution of urea and sodium hydroxide (0.5M urea in 5% NaOH). This yielded a 1:1 molar ratio of chlorine to urea as shown in Table 3. We then blended 5.0 mL NaOCl (3% as $Cl_2$ in water) with 5.0 mL of an aqueous solution of urea and sodium hydroxide (0.25M urea in 5% NaOH). This yielded a 2:1 molar ratio of chlorine to urea.

Paper process water was collected from a mill in the Northeastern US producing coated groundwood printing and writing grades (pH 7.9). Samples were dosed with halogen and plated after one and four hours. Following the four-hour sampling, process water was challenged with 1% (volume/volume) of untreated process water and samples were plated again after 24 hours. The results are outlined in Table 4.

TABLE 4

| | | Bacterial Density (log 10 CFU/mL) | |
|---|---|---|---|
| Solution | Contact Time (hours) | 2.5 ppm Total $Cl_2$ | 10 ppm Total $Cl_2$ |
| NaOCl, pH 9.8 | 1 | 2 | 2 |
| | 4 | 3.5 | 2 |
| | 24 | 7.4 | 7.3 |
| NaOCl:Urea (2:1 mole ratio), pH 13.3 | 1 | 3.1 | 3 |
| | 4 | 3.1 | 2 |
| | 24 | 7.2 | 7.3 |
| NaOCl:Urea (1:1 mole ratio), pH 13.4 | 1 | 2 | 2 |
| | 4 | 2.5 | 2 |
| | 24 | 5.2 | 2 |

Urea at 1:1 mole ratio with NaOCl, in this experiment, significantly enhanced the bactericidal activity of NaOCl against bacteria native to the process water sample even in this high chlorine demand furnish sample. Mixing NaOCl and urea at a 1:1 mole ratio improved the persistence of the antimicrobial efficacy following a challenge with untreated process water when compared to NaOCl alone and NaOCl mixed with urea at a 2:1 mole ratio.

Example 5

At effective antimicrobial concentrations, urea improved compatibility of NaOCl with optical brightening agents compared to NaOCl alone. We blended 8.4 mL NaOCl (6.3% as $Cl_2$ in water) with 1.5 mL of an aqueous solution of urea and sodium hydroxide (2.5M urea in 20% NaOH). This yielded a 2:1 molar ratio of chlorine to urea as shown in Table 5. We then blended 7.3 mL NaOCl (6.3% as $Cl_2$ in water) with 2.7 mL of an aqueous solution of urea and sodium hydroxide (2.5M urea in 20% NaOH). This yielded a 1:1 molar ratio of chlorine to urea as shown in Table 5.

The absorbance (350 nm) of Leucophor AP at 50 ppm was measured in buffered water with and without exposure to halogen after 60 minutes. Results are outlined in Table 5.

TABLE 5

| Solution | Concentration (ppm Total $Cl_2$) | % Absorbance Relative to Untreated Control Leucophor AP |
|---|---|---|
| NaOCl, pH 9.8 | 2.5 | 60 |
| | 5 | 41 |
| | 10 | 24 |
| NaOCl:Urea (2:1 mole ratio), pH13.3 | 2.5 | 90 |
| | 5 | 85 |
| | 10 | 79 |
| NaOCl:Urea (1:1 mole ratio), pH 13.4 | 2.5 | 100 |
| | 5 | 100 |
| | 10 | 99 |

Improved compatibility with optical brightening agents is very beneficial because it allows higher $Cl_2$ dose concentrations, if necessary, for improved control of microorganisms, while reducing native impacts on other performance additives. Blending NaOCl and urea at a molar ratio of 1:1 significantly improved compatibility of the resulting stabilized chlorine relative the blending at a 2:1 molar ratio.

Example 6

At effective antimicrobial concentrations, NaOCl blended with chlorine at an elevated pH reduced vapor-phase corrosion of carbon steel compared to NaOCl alone. The unstabilized bleach solution was 3% as $Cl_2$ in water. To prepare the stabilized chlorine solution we blended 5.0 mL NaOCl (3% as $Cl_2$ in water) with 5.0 mL of an aqueous solution of urea and sodium hydroxide (0.5M urea in 5% NaOH). This yielded a 1:1 molar ratio of chlorine to urea as shown in Table 6. We then blended 5.0 mL NaOCl (3% as $Cl_2$ in water) with 5.0 mL of an aqueous solution of urea and sodium hydroxide (0.25M urea in 5% NaOH). This yielded a 2:1 molar ratio of chlorine to urea. Results are outlined in Table 6.

TABLE 6

| Solution | Concentration (ppm Total $Cl_2$) | Vapor-Phase Corrosion (mpy) |
| --- | --- | --- |
| NaOCl, pH 9.8 | 1 | 1.8 |
|  | 2.5 | 1.7 |
| NaOCl:Urea | 1 | 0.9 |
| (2:1 mole ratio), | 2.5 | 1.3 |
| pH 13.3 |  |  |
| NaOCl:Urea | 1 | 0.2 |
| (1:1 mole ratio), | 2.5 | 0.3 |
| pH 13.4 |  |  |

Reduced corrosion rates are very beneficial. This can allow for the use of higher $Cl_2$ dose concentrations, if necessary, to improve control of microorganisms, while reducing corrosion of metal components in or near the treated system. Blending NaOCl and urea at a molar ratio of 1:1 significantly reduced vapor-phase corrosion rates of the resulting halogen solution relative to blending at a 2:1 molar ratio. This further protects the equipment used.

That which is claimed is:

1. A method for stabilizing chlorine for use as a water treatment biocide in a papermaking process system, comprising the steps of:
    adding, with mixing, a free chlorine source to a point in a stream of the papermaking process system;
    adding, with mixing, urea to a point in the stream of the papermaking process system; and
    adding, with mixing, an alkali to a point in the stream of the papermaking process system, to cause mixing of the alkali with the chlorine source and the urea;
    wherein the result of the additions causes to be formed for a period of time within the papermaking process stream a composition, the composition comprising: a free chlorine-generating biocide comprising a chlorine source; urea; and an alkali in a concentration sufficient to provide a pH of from 12 to 13.5 for said composition, and wherein the composition does not comprise stabilized bromine.

2. The method of claim 1 in which the chlorine source, the urea, and the alkali are all added to points in the stream of the process system which are the same or adjacent to each other.

3. The method of claim 1 in which the chlorine source and the alkali are premixed and added to the stream of the process system together, and the urea is separately added to the stream of the process system.

4. The method of claim 1 in which the chlorine source, the urea, and the alkali are all separately added to the stream of the process system.

5. The method of claim 4 in which the free chlorine source is added to the stream of the paper process system intermittently, and the urea and the alkali are added continuously.

6. The method of claim 1 in which said chlorine source comprises an aqueous solution of sodium hypochlorite having approximately 5-15 weight percent of chlorine (based on $Cl_2$) plus sufficient sodium hydroxide to provide a pH of at least 11 in the zone of mixing with urea.

7. The method of claim 1 in which said urea comprises an aqueous urea solution, in a concentration within about 20% of the solubility limit for urea in the solution at the temperature at which solution is used.

8. The method of claim 1 in which the chlorine source and the urea used are present in a molar ratio of 2:1-1:2, the chlorine being calculated as $Cl_2$.

9. The method of claim 1 in which said chlorine source is present in a concentration sufficient to provide essentially an equimolar amount of chlorine, expressed as $Cl_2$, to the urea present.

10. The method of claim 1 in which said chlorine source is selected from the group consisting of: calcium hypochlorite; sodium hypochlorite; dichloroisocyanurate; trichloroisocyanurate; dichlorohydantoin; and $Cl_2$.

11. The method of claim 1 in which said alkali comprises sodium hydroxide or potassium hydroxide.

12. The method of claim 1 in which the chlorine source is added to the stream of the paper process system intermittently, and the urea and the alkali are added to the process stream intermittently.

13. The method of claim 1 in which the free chlorine source is added to the stream of the paper process system continuously, while the urea and the alkali are added continuously.

14. The method of claim 1 in which the free chlorine source is added to the stream of the paper process system continuously, and the urea and the alkali are added intermittently.

* * * * *